(12) United States Patent
Montessuy et al.

(10) Patent No.: US 9,320,501 B2
(45) Date of Patent: Apr. 26, 2016

(54) SURGICAL INSTRUMENT FOR MOLECULAR SAMPLING

(75) Inventors: Renaud Montessuy, Eybens (FR);
David Ratel, Saint-Peray (FR);
Emmanuel Gay, Corenc (FR);
Jean-Guy Passagia, Vaulnaveys le Haut (FR); François Berger, Meylan (FR);
Jean-Paul Issartel, Saint Egreve (FR)

(73) Assignees: Universite Joseph Fourier—Grenoble 1, St. Martin d'Heres (FR);
Commissariat a L'Energie Atomique et Aux Energies Alternatives, Paris (FR); Centre Hospitalier Universitaire de Grenoble, La Tronche (FR)

( * ) Notice: Subject to any disclaimer, the term of this patent is extended or adjusted under 35 U.S.C. 154(b) by 0 days.

(21) Appl. No.: 13/496,635

(22) PCT Filed: Sep. 16, 2010

(86) PCT No.: PCT/EP2010/063587
§ 371 (c)(1),
(2), (4) Date: Mar. 16, 2012

(87) PCT Pub. No.: WO2011/033008
PCT Pub. Date: Mar. 24, 2011

(65) Prior Publication Data
US 2012/0172753 A1    Jul. 5, 2012

(30) Foreign Application Priority Data

Sep. 18, 2009    (FR) ...................................... 09 56419

(51) Int. Cl.
*A61B 10/00*     (2006.01)
*A61B 10/02*     (2006.01)
(Continued)

(52) U.S. Cl.
CPC ....... *A61B 10/02* (2013.01); *A61B 2017/00738* (2013.01); *A61B 2017/3419* (2013.01); *A61B 2017/3456* (2013.01); *A61B 2019/306* (2013.01)

(58) Field of Classification Search
CPC ............. A61B 10/02; A61B 2019/306; A61B 2017/3456; A61B 2017/3419
USPC ................. 600/562, 564, 567, 569, 570, 572; 606/167, 170
See application file for complete search history.

(56) References Cited

U.S. PATENT DOCUMENTS 3,857,384 A    12/1974  Watson
3,877,464 A     4/1975  Vermes
(Continued)

FOREIGN PATENT DOCUMENTS

EP      1724579 A2     11/2006
WO   2006082344 A1      8/2006
(Continued)

OTHER PUBLICATIONS

Cosnier et al., "A new micro minimally invasive biopsy tool for molecular analysis", Proceedings of the 28th IEEE, EMBS Annual International Conference, New York City, USA, Aug. 30-Sep. 3, 2006.
(Continued)

*Primary Examiner* — Max Hindenburg
*Assistant Examiner* — Jonathan M Foreman
(74) *Attorney, Agent, or Firm* — Harness, Dickey & Pierce, P.L.C.

(57) ABSTRACT

The present disclosure relates to a surgical instrument for sampling molecules in an organ which can be accessed directly or via a surgical portal, including:
  a device for capturing the molecules,
  a stylet supporting the capture device, capable of entering the organ,
  a guide for inserting the stylet into the body as far as the organ, wherein the distal end of the guide is provided with a damping block intended to come to bear upon the organ.

20 Claims, 4 Drawing Sheets

(51) Int. Cl.
*A61B 17/00* (2006.01)
*A61B 17/34* (2006.01)
*A61B 19/00* (2006.01)

(56) References Cited

U.S. PATENT DOCUMENTS

| | | | |
|---|---|---|---|
| 3,995,618 A | 12/1976 | Kingsley et al. | |
| 4,157,709 A * | 6/1979 | Schuster et al. | 600/572 |
| 4,628,941 A * | 12/1986 | Kosasky | 600/572 |
| 4,742,829 A * | 5/1988 | Law et al. | 600/461 |
| 5,031,635 A * | 7/1991 | Koll | 600/569 |
| 5,090,414 A * | 2/1992 | Takano | 600/461 |
| 5,129,402 A | 7/1992 | Koll et al. | |
| 5,370,129 A * | 12/1994 | Diaz et al. | 128/839 |
| 5,415,182 A * | 5/1995 | Chin et al. | 600/567 |
| 5,474,075 A * | 12/1995 | Goldberg et al. | 600/463 |
| 5,830,154 A | 11/1998 | Goldstein et al. | |
| 6,155,990 A | 12/2000 | Fournier | |
| 6,336,905 B1 * | 1/2002 | Colaianni | 600/569 |
| 6,921,370 B2 | 7/2005 | Zhou et al. | |
| 8,152,736 B2 * | 4/2012 | Caillat et al. | 600/562 |
| 2002/0095073 A1 | 7/2002 | Jacobs et al. | |
| 2003/0028123 A1 | 2/2003 | Pevoto | |
| 2007/0003989 A1 | 1/2007 | Ellingsen et al. | |
| 2009/0280523 A1 | 11/2009 | Benabid et al. | |
| 2010/0049083 A1 | 2/2010 | Caillat et al. | |
| 2010/0168609 A1 | 7/2010 | Pison et al. | |
| 2011/0213270 A1 | 9/2011 | Pison | |

FOREIGN PATENT DOCUMENTS

| | | |
|---|---|---|
| WO | 2006090220 A2 | 8/2006 |
| WO | 2008110392 A2 | 9/2008 |
| WO | 2010025719 A1 | 3/2010 |

OTHER PUBLICATIONS

Ali Bouamrani et al., "Direct-Tissue SELDI-TOF Mass Spectrometry Analysis: a new application for clinical proteomics", Clinical Chemistry 52, No. 11, 2006, pp. 2103-2106.

Cosnier et al., IEEE, available on-line on: Jul. 14, 2009: A minimally invasive micro-device for molecular sampling and analysis.

* cited by examiner

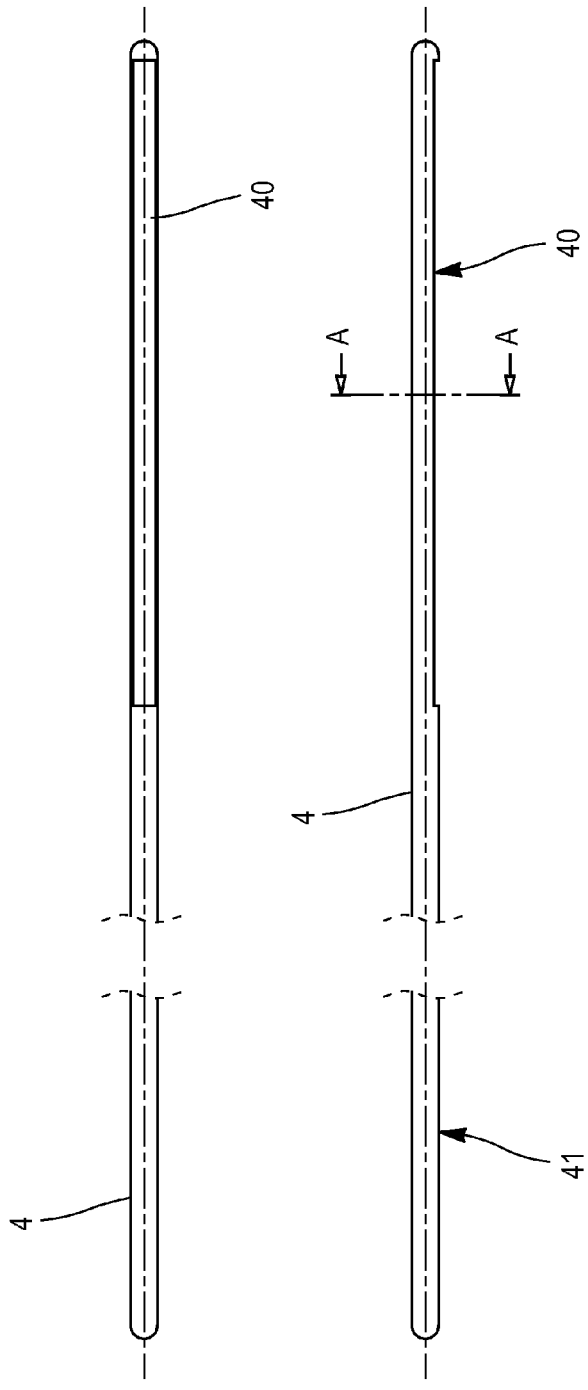

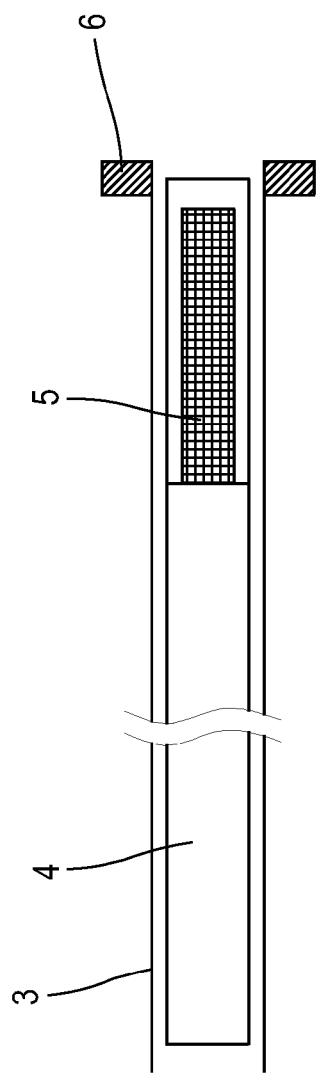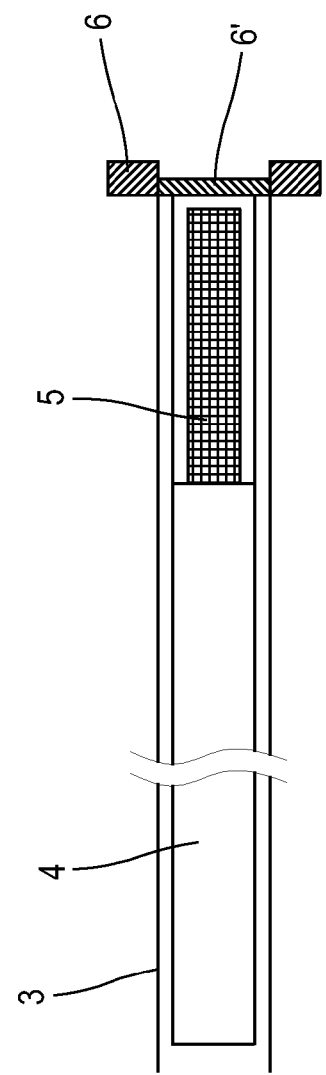

SURGICAL INSTRUMENT FOR MOLECULAR SAMPLING

CROSS-REFERENCE TO RELATED APPLICATIONS

This application is a National Phase Entry of International Application No. PCT/EP2010/063587, filed on Sep. 16, 2010, which claims priority to French Patent Application Serial No. 0956419, filed on Sep. 18, 2009, both of which are incorporated by reference herein.

FIELD

The present invention relates to a surgical instrument for molecular sampling, comprising a guide and a stylet supporting a device for capturing molecules.

BACKGROUND

The capturing of biomarkers in a patient's body is useful for diagnosing and locating lesions such as tumours. Biomarkers are molecules e.g. proteins which are specific to the lesion under consideration. For example the ACTH protein is a biomarker of pituitary corticotrope adenoma or Cushing's disease.

Before or during surgical procedure on the lesion, it is generally necessary to identify with precision the contours of this lesion, so that it can be entirely removed without removing healthy tissue. The capture of biomarkers pre- or per-operatively is currently the subject of experimental studies for some surgical procedures. For example, mention may be made of intra-cranial molecular biopsy by stereotaxy for the diagnosis of gliomas. This procedure consists of inserting in the patient's head, via a stereotactic frame, a stylet provided at its distal end with an activated silicon wafer to capture the molecule(s) to be identified. Since this technique assumes the passing through several tissues, it is necessary to protect the silicon wafer against any contamination aside from the lesion itself.

It has therefore been proposed in document WO 2006/090220, to provide a guide enclosing the stylet and allowing the sliding and rotation of the stylet within the guide. The guide, at its distal end, has a window formed of an opening made in the wall thereof. When being inserted through the skull, the stylet is positioned in the guide so that the activated side of the silicon wafer lies opposite the window, thereby being protected. When the tip of the guide has reached its target, the surgeon rotates the stylet through about 180° so that the activated side of the silicon wafer is exposed. After the time required for capturing the molecules, the surgeon again rotates the stylet through about 180° within the guide, so that the activated side of the silicon wafer is again protected for the return pathway of the stylet.

However, this instrument has limitations, in particular in terms of volume and use. The need to arrange a guide around the stylet effectively increases the volume of the instrument. The outer diameter of the instrument inserted in the tissues is therefore of the order of 2 to 5 mm.

In addition, it cannot be used for the treatment of some pathologies, in particular for the detection of pituitary adenoma (or Cushing's disease). The pituitary gland is located at a point which would require the perforating of several particularly sensitive organs in order to have access thereto via this route. Also, since it is desired to capture the ACTH protein for more precise location of the lesion, with a view to removal during the same surgical procedure, the stereotactic approach described in the above-mentioned document is of little interest.

At the current time it is also known to perform one or more extemporaneous biopsies, by removing tissues from the regions of interest of the organ under consideration for the purpose of analysis during surgery. However, this technique is aggressive. On the contrary, it is sought to use minimally invasive procedures.

It is therefore the objective of the present invention to provide an instrument for minimally invasive molecular capture allowing the replacement of biopsy via stereotactic route when this cannot be envisaged, that is particularly suited for intra-pituitary sampling. It is a further objective of the invention to provide an instrument of smaller volume than in the prior art.

SUMMARY

According to the invention, a surgical instrument is provided for sampling molecules from an organ which can be accessed directly or via a surgical portal, comprising:
  a device for capturing said molecules,
  a stylet supporting said capture device and capable of entering the organ,
  a guide for inserting the stylet into the body as far as the organ,
said instrument being characterized in that the distal end of the guide is provided with a damping block intended to bear against the member.

In the present text by "distal end" is meant the end of the instrument which is inserted into the patient's body, towards the target organ; and by "proximal end" the end handled by the surgeon. By "directly accessible organ" in the present text is meant any organ in which it is possible to capture the biomarkers without previously passing through other organs.

The invention also concerns the sampling of organs whose access is possible via a previously opened portal, i.e. once the portal is opened the instrument does not have to pass through any tissues to reach the organ. According to other advantageous characteristics of the invention:
  the distal end of the stylet is also provided with a damping block arranged so as to ensure sealing with respect to the guide;
  the damping block is made in a biocompatible, non-protein polymer material;
  with respect to the organ, the damping block has a coefficient of friction higher than steel;
  the molecule capture device is arranged in a housing of the distal portion of the stylet so that only its active side is exposed;
  the capture device is adapted to capture proteins but also, when applicable, any other biological material;
  the stylet and/or guide is provided with a neuro-navigational sensor;
  the instrument comprises an adjustable abutment to control the depth of insertion of the stylet into the organ;
  the instrument comprises several parallel guides for simultaneous sampling of molecules at different points of the organ, the distal end of each guide being provided with a damping block that is individual or common to all the guides.

BRIEF DESCRIPTION OF THE DRAWINGS

Other characteristics and advantages of the invention will become apparent from the following description given with reference to the appended drawings in which:

FIG. 2 is an overhead view of the stylet;

FIG. 3 is a profile view of the stylet;

FIG. 4 is an (enlarged) cross-section of the stylet along section A-A- in FIG. 3;

FIG. 5 is an (enlarged) left-hand view of the stylet illustrated in FIG. 3;

FIGS. 6A and 6B illustrate two embodiments of the damping blocks; and

DETAILED DESCRIPTION

The present invention will now be described in detail, but in non-limiting manner, with reference to the capture of biomarkers in the pituitary gland, in particular for identification of the ACTH protein (adenocorticotrope hormone) which is a specific marker of pituitary corticotrope adenoma or Cushing's disease. The pituitary gland is located directly behind the sphenoid. Pituitary adenoma therefore follows the transsphenoid route, which involves passing through the nasal fossae, through a pathway that is first deep and narrow before leading into the sphenoid sinus, giving access to the pituitary fossa.

However, the pituitary gland is directly accessible i.e. it is not necessary to pass through tissues to reach it once the portal has been made. As a result, contrary to the stereotactic capture device mentioned in the preamble, the capture device runs a lesser risk of being contaminated as it passes through the patient's body before reaching the pituitary gland. It is therefore possible to dispense with the window device and to propose an organ-entering device that is less cumbersome than the prior art device. However, having regard to the major bleeding generated during this procedure, it is necessary to ensure the sealing of the device against this bleeding.

Figure 1:
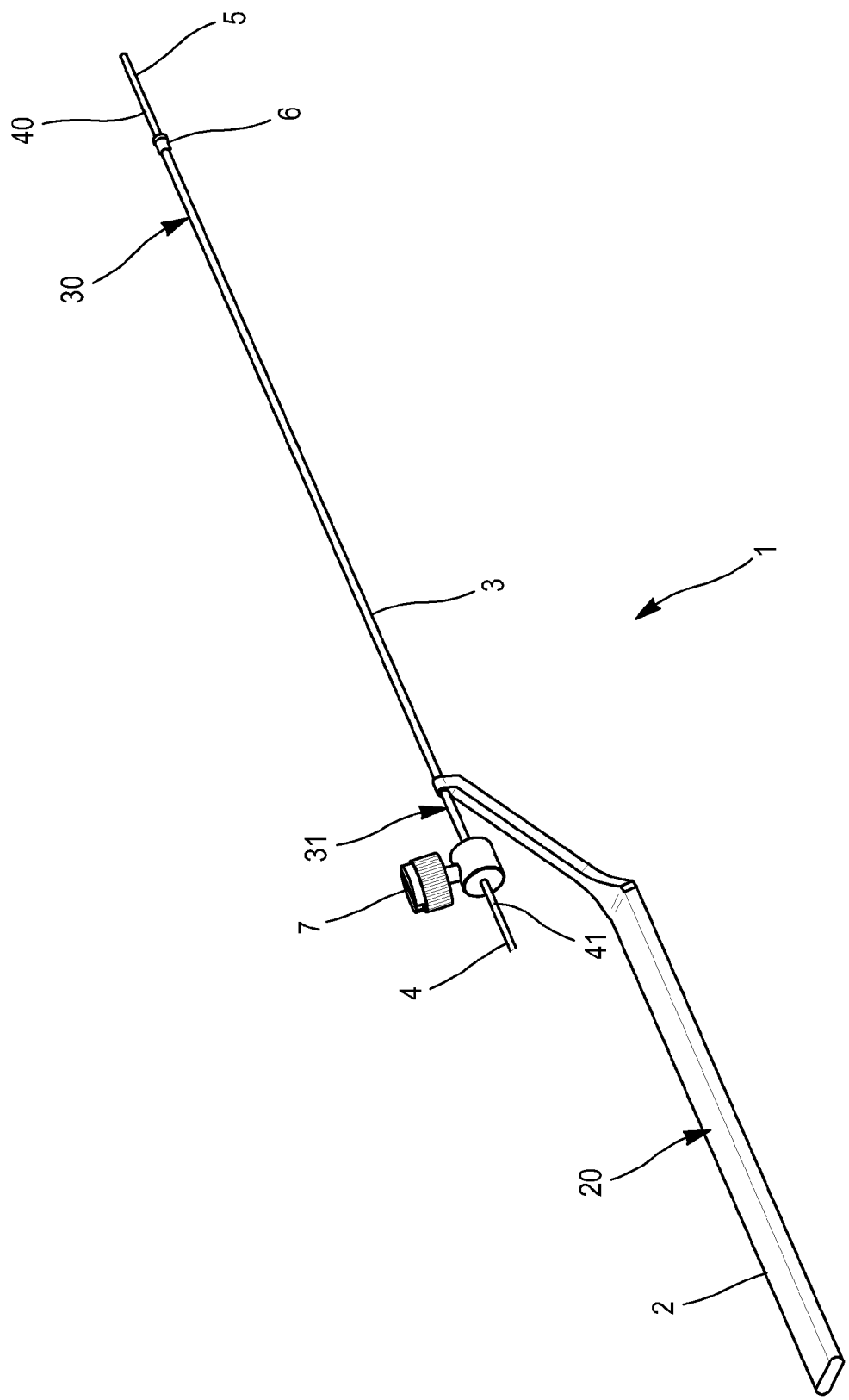
FIG. 1 is an overall view of the instrument conforming to the invention, in sampling position.

FIG. 1 gives an overall view of the instrument. As can be seen, the instrument 1 comprises a support 2 adapted to be grasped by the surgeon, the support 2 being extended by a guide 3 in which a stylet 4 is slidingly mounted carrying a capture device 5 at its distal end.

Guide and Support

The guide 3 is in the general form of a tube and has a distal portion 30 intended to be inserted into the patient's body. The inner diameter of the guide 3 is adapted for the inserting and sliding of the stylet 4. Typically, the inner diameter of the guide is 900 µm, and the outer diameter of the stylet is of the order of 800 µm.

In its proximal portion 31, the guide 3 is connected to the support 2. For example the guide 3 and the support 2 are both metallic, and the guide 3 is inserted in a borehole provided for this purpose on the support 2 and is then laser welded. Of course, any other assembly mode of the guide 3 and support 2 can be envisaged—even their unitary structure or on the contrary their dismountable structure (to allow the use of several guides during a procedure, for example when a guide is contaminated). Advantageously, the guide 3/support 2 assembly is of bayonet shape i.e. the grasping portion 20 and the guide 3 have substantially parallel axes but offset by a few centimeters from each other. The viewing of the distal end 30 of the guide 3 is therefore not hampered by the surgeon's hand when manipulating the instrument 1.

Stylet

With reference to FIGS. 2 to 5, the stylet 4 is of general cylindrical shape, except at its distal end where it comprises a housing 40 for the molecular capture device and at its proximal end where it comprises a reference flat face 41. The instrument 1, in its proximal portion, is provided with an adjustable abutment 7 which allows limiting of the depth of insertion of the stylet 4 in relation to the distal end of the guide 3. Both the stylet 4 and the guide 3 are made in biocompatible materials, such as surgical stainless steel for example, or any other biocompatible metal whether or not ferromagnetic.

Capture Device

The capture device 5 is in the general shape of a wafer comprising a surface containing activated chemical groups for capturing the desired molecules. For example, silicon chips may be used such as described in documents WO 2006/082344 and "A new micro minimally invasive biopsy tool for molecular analysis", Cosnier et al., Proceedings of the $28^{th}$ IEEE, EMBS Annual Conference, New York City, USA, Aug. 30-Sep. 3, 2006, but also any other substrate adapted for adsorption of the molecules under consideration can be used.

The dimensions of the capture device are typically: length of 20 mm, width of 650 µm and a thickness of 300 µm. Evidently, it is possible to use a capture device having a shape other than rectangular and having other dimensions. In addition, the capture device can be divided into different zones, each zone able to give an indication for different depths of the organ. Since the silicon wafer has sharp edges, and therefore may harm the walls of the cavities through which it passes, it is inserted in a housing 40 arranged for this purpose in the stylet 4. The capture device 5 is removably fixed on the stylet 4 using any suitable means such as gluing, press-fitting, screwing, etc.

The housing 40 can be better seen in FIG. 4 in which it can be seen that it is formed of a cut-out of rectangular shape in the cross-section of the stylet 4. The housing 40 has dimensions that are substantially equal to the dimensions of the capture device but slightly larger to facilitate the mounting and dismounting of the capture device. The edges of the capture device (not illustrated in FIG. 4) are therefore protected by the walls of the housing 40.

The housing 40 has the additional advantage of protecting the capture device 5 against undue separating from the stylet when the instrument is inside the patient's body. The housing 40 and hence the capture device 5 are located in a position that is the most distal possible from the stylet 4 (i.e. a typical distance of 400 to 600 µm relative to the distal end of the stylet) so as to provide the largest contact surface possible with the target organ. With reference to FIG. 5, the stylet 4, at its proximal end, comprises a flat part 41 used for identifying the position of the housing 40. This flat part 41 for example lies at a distance of 200 µm from the axis of the stylet.

Damping Block

The distal end of the guide 3 is provided with a damping block 6 intended to come to bear upon the organ without penetrating inside the organ. The contact surface of the damping block 6 against the organ is typically ring-shaped with a diameter generally less than 2.5 mm, the block 6 having to allow the passing of the distal end of the stylet 4 for capturing of the molecules.

In particularly advantageous manner, the damping block 6 is made in a biocompatible, non-protein polymer material, for example in silicone. The block 6 is made in material that is sufficiently flexible and deformable, and at its distal end it has sufficient surface area to ensure contact with the organ and to dampen any impact when the guide 3 abuts the organ.

The block 6 is also designed so as not to have any sharp edges. Preferably, it also has anti-skid properties thereby allowing the limited movement of the instrument in relation to the organ as sampling proceeds. For example, the coefficient of friction of the block 6 on the organ is higher than the coefficient of friction of steel on the organ.

Finally, the damping block 6 ensures a sealing function against any blood contamination. According to a first embodiment, (schematically illustrated in FIG. 6A) only the distal end of the guide 3 is provided with said block 6. According to one variant of embodiment (schematically illustrated in FIG. 6B) the distal end of the stylet 4 is also capped with a block 6' similar to block 6. Preferably the block 6' is profiled e.g. nose-shaped to facilitate the insertion of the stylet into the organ. This provides better protection for the capture device 5 against surrounding bleeding.

The block 6, and when applicable 6', is secured to the guide 3, respectively onto the stylet 4, so as to avoid any undue separation thereof when they are inside the patient's body. According to one particular embodiment, a silicone block is press-fitted around the metallic part (guide or stylet). It is also possible for example to use glue having suitable adhesion with the block material and guide material (and optionally the stylet material).

Multi-Sampling Instrument

According to one variant of embodiment (not illustrated), the support is able to support several parallel guides intended to be inserted simultaneously as far as the organ, each guide being provided with a damping block as described above. Alternatively, instead of individual damping blocks arranged at the distal end of each guide, a single block of suitable shape can be arranged at the distal end of the assembly of guides so that it is common thereto. A stylet is then inserted into each of the guides, which allows simultaneous sampling at several points of the organ, hence notable savings in time for the procedure.

Neuro-Navigation

Although the target organ is visible and accessible to the surgeon without medical imaging, it may be advantageous to locate the capture device in an image in which the lesion is also visible. This makes it possible to define more precisely the pathway of the guide and stylet for better precision targeting of the sampling area. For this purpose, the stylet and/or the guide can be equipped with a sensor allowing determination of the position of the stylet in the reference frame of the image.

For example, infrared diodes can be assembled on the guide and a dismountable diode (forming an equivalent system to the abutment) on the stylet. The relative movement of this diode in relation to the others allows depth locating, whereas the diodes of the guide provide information on the positioning and pathway via an appropriate camera transmitting this data to the neuro-navigation system.

Use of the Instrument

During surgical procedure intended to capture the ACTH protein, the biomarker of pituitary adenoma, the instrument 1 is used in the following manner. First the surgeon inserts the guide 3 inside the patient's nasal cavity then the sphenoid until it reaches the pituitary gland. On account of the bayonet shape of the support 2, the surgeon's visual field is free and the pituitary gland can be seen directly. Alternatively, when the guide 3 and/or stylet 4 are visible in a neuro-navigational tool, the surgeon verifies the pathway of the guide in the image.

Once the guide 3 has abutted the gland via the damping block 6, the surgeon inserts therein the stylet 4 provided with the capture device 5 at its distal end. In this case, the stylet can be accompanied by a mandrel in the guide. It is also possible to insert the guide into the patient's organ when the stylet is already inserted in the guide, in particular if the stylet is provided with a damping block or if there is a short distance between the microscope and the instrument.

Figure 7:
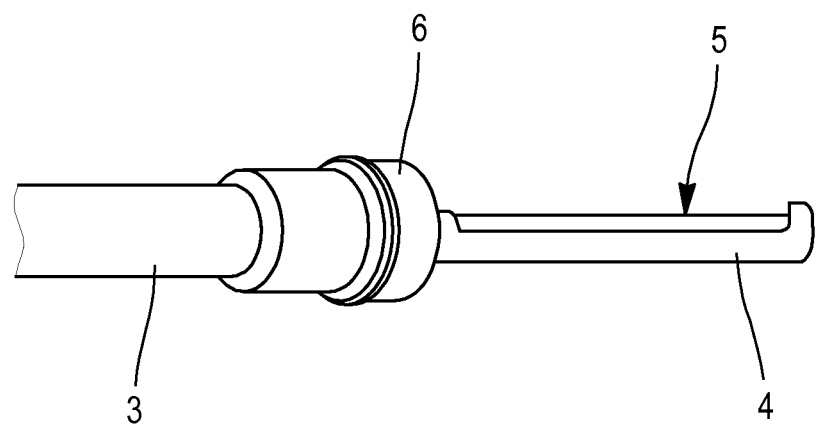
FIG. 7 is a detailed view of the distal end of the guide and stylet in sampling position.

The distal end of the stylet 4 then emerges from the distal end of the guide 3 and perforates the gland until it reaches the abutment 7 thereby placing the capture device 5 in contact with gland tissue, and allowing capture of the ACTH protein. This situation is illustrated in FIG. 7. On this account only the distal end of the stylet comprising the capture device of the instrument, which has a maximum diameter of 800 μm, is inserted in the tissue. The abutment 7 prevents the stylet 4 from being inserted too deep into or through the pituitary gland, which is of small size (of the order of 1 cm in an adult person).

After a time that is sufficient for capturing a significant quantity of molecules (typically 10 to 30 seconds) the surgeon removes the stylet and the guide, or else slightly offsets the guide and inserts a new stylet to take a sample at a different point of the pituitary gland. Once the samples have been taken, the capture device 5 is then dismounted from the stylet 4 using any suitable means depending on the securing mode used, for the purpose of detecting the ACTH protein. It will therefore be understood that the instrument just described has the advantage of minimising the aggressiveness of intra-pituitary surgical techniques, achieving more precise excision. This makes it possible to limit post-operative endocrine deficiencies and surgical morbidity.

Detection of the Captured Molecules

Once the capture device 5 has been dismounted from the stylet 4, the detection of the molecules can be carried out using different techniques. According to a first possibility, the adsorbed biomarkers are eluted and the quantity of these molecules in the solution obtained is measured. Another particularly advantageous technique consists of placing the capture device in a mass spectrometry system such as the one described in document WO 2006/090220 for example. The advantage of this technique is to allow the direct reading of the quantity of adsorbed molecules.

Although the invention has been chiefly described for application to the capture of the biomarkers of a pituitary tumour, it also applies to the capture of molecules in another organ that is directly accessible. The present invention therefore finds application in the capture of biomarkers of ENT tumours (ear-nose-throat), skin and muscle tumours, or gynaecological tumours. It is also of interest in infectious pathologies (diagnosis of abscesses for example).

The invention claimed is:

1. A surgical instrument for sampling molecules in an organ which can be accessed directly or via a surgical portal, comprising:
    a capture device comprising a wafer having a surface with activated chemical groups for capturing the molecules,
    an elongated stylet capable of entering the organ, the stylet comprising a circumferential cylindrical wall extending between a distal end and a proximal end, the stylet supporting said capture device within the circumferential wall of the stylet adjacent the distal end,
    a guide for inserting the stylet into the body as far as the organ, the guide defining a bayonet shape such that an axis of the guide is offset relative to an axis of the elongated stylet,
    wherein the distal end of the guide is provided with a damping block intended to come to bear upon the organ;
    wherein an outer diameter of the ring-shaped damping block is less than 2.5 mm;
    wherein the damping block seals around the distal end of the guide and onto the stylet; and wherein the damping block is made of a biocompatible, non-protein polymer material.

2. The instrument of claim 1, wherein the damping block in relation to the organ has a coefficient of friction higher than that of steel.

3. The instrument of claim 1, wherein the capture device is arranged in a housing of the distal portion of the stylet, so that only its active side is exposed.

4. The instrument of claim 1, wherein the capture device is adapted to capture proteins or any other biomolecule.

5. The instrument of claim 1, wherein the stylet and/or the guide is provided with a neuro-navigational sensor.

6. The instrument of claim 1, further comprising an adjustable abutment to control the depth of insertion of the stylet into the organ.

7. The instrument of claim 1, wherein the wafer is made of silicon.

8. The instrument of claim 1, wherein the distal end of the stylet has a diameter smaller than 800 µm.

9. The instrument of claim 1, further comprising an elongated and doctor-graspable support coupled to the guide by a neck which is thinner than the support, the support including an elongated flat surface.

10. The instrument of claim 1, wherein the guide is metallic, straight and has a uniform cross-sectional diameter.

11. A surgical instrument comprising:
a stylet having a generally cylindrical shape, comprising a housing arranged lengthwise in a distal region thereof;
a silicon wafer arranged in the housing of the stylet such that the edges of the wafer are located inside the housing, the wafer comprising an exposed surface containing activated chemical groups;
a cylindrical guide wherein the stylet is slidingly mounted, the cylindrical guide having a bayonet shape such that an axis of the stylet is offset from an axis of an elongated and doctor-graspable support coupled to the guide by a neck which is thinner than the support, the support including an elongated flat surface; and
a ring-shaped deformable block arranged at the distal end of the guide;
wherein the wafer is removably fixed in a recessed housing in the stylet such that edges of the wafer are protected by walls of the stylet housing;
wherein the deformable block seals around the distal end of the guide and onto the stylet.

12. The instrument of claim 11, wherein the deformable block protects the wafer against blood contamination when the distal region of the stylet is within the guide.

13. The instrument of claim 11, wherein the deformable block arranged at the distal end of the guide is ring-shaped so as to allow the passing of the distal portion of the stylet.

14. The instrument of claim 11, wherein an outer diameter of the ring-shaped deformable block is less than 2.5 mm.

15. The instrument of claim 11, wherein the guide is metallic, straight and has a uniform cross-sectional diameter.

16. A surgical instrument comprising:
an elongated and straight stylet adapted to enter an organ, the stylet including a biomarker capturing-wafer at an end thereof;
activated chemical groups located on the wafer, and the wafer being a silicon material;
an elongated support adapted for surgeon-grasping;
a guide coupled to the support and the stylet being slidably mounted to the guide, the support being parallel to but offset from the guide; and
a damping block including an organ-contacting surface having a ring-shape with a diameter less than 2.5 mm, the block allowing the end of the stylet to pass therethrough, the block having anti-skid properties adapted to limit movement of the instrument in relation to the organ if sampling is occurring, the block being adapted to seal against an adjacent organ or tissue to deter blood contamination when used, the block being deformable, and the block surrounding a distal end of the guide and onto a portion of the stylet extending therefrom.

17. The instrument of claim 16, wherein the block is a flexible polymeric material, the capture wafer is no bigger than 20 mm in length, 650 µm in width and 300 µm in thickness, and the diameter of the end of the stylet adapted to enter the organ is less than 800 µm.

18. The instrument of claim 16, further comprising a diagonally angled neck coupling the support to the guide, the neck being thinner than the support, and the support including an elongated flat surface.

19. The instrument of claim 16, wherein the wafer is removably fixed in a recessed housing in the stylet such that edges of the wafer are protected by walls of the stylet housing, and the wafer includes silicon.

20. The instrument of claim 16, wherein the guide is metallic, straight and has a uniform cross-sectional diameter.

* * * * *